United States Patent [19]

Hassler et al.

[11] Patent Number: 5,009,232

[45] Date of Patent: Apr. 23, 1991

[54] EXTRACORPOREAL LITHOTRIPSY APPARATUS USING HIGH INTENSITY SHOCK WAVES FOR CALCULUS DISINTEGRATION AND LOW INTENSITY SHOCK WAVES FOR IMAGING

[75] Inventors: Dietrich Hassler, Uttenreuth; Erhard Schmidt, Erlangen, both of Fed. Rep. of Germany

[73] Assignee: Siemens Aktiengesellschaft, Munich, Fed. Rep. of Germany

[21] Appl. No.: 392,356

[22] Filed: Aug. 11, 1989

[30] Foreign Application Priority Data

Aug. 17, 1988 [EP] European Pat. Off. ........ 88113375.5

[51] Int. Cl.⁵ .............................................. A61B 17/22
[52] U.S. Cl. ............................ 128/660.03; 128/24 EL
[58] Field of Search ...................... 128/660.03, 24 EL

[56] References Cited

U.S. PATENT DOCUMENTS

| | | |
|---|---|---|
| 3,913,061 | 10/1975 | Green . |
| 4,131,021 | 12/1978 | Mezrich et al. . |
| 4,526,168 | 7/1985 | Hassler et al. ..................... 128/24 A |
| 4,674,505 | 6/1987 | Pauli et al. . |
| 4,771,787 | 9/1988 | Wurster et al. . |
| 4,803,995 | 2/1989 | Ishida et al. ..................... 128/660.03 |
| 4,834,106 | 5/1989 | Hassler et al. . |

FOREIGN PATENT DOCUMENTS

| | | |
|---|---|---|
| 0254104 | 1/1988 | European Pat. Off. . |
| 2722252 | 4/1979 | Fed. Rep. of Germany . |
| 2187840 | 9/1987 | United Kingdom ........... 128/660.03 |

Primary Examiner—Ruth S. Smith
Attorney, Agent, or Firm—Hill, Van Santen, Steadman & Simpson

[57] ABSTRACT

An apparatus for extracorporeal lithotripsy includes a shock wave source which generates shock waves converging in focus a zone, within which a calculus to be disintegrated is disposed. The shock wave source can be selectively driven to generate high-intensity shock waves for disintegrating the calculus, and for generating low-intensity shock waves for imaging purposes. A pressure sensor is disposed between the focus zone and the shock wave source to register the reflections of the low-intensity shock waves. The pressure sensor has a sensor surface which is substantially coextensive with the cross-sectional area of the shock waves in the region of the pressure sensor, and is connected to a reception circuit which constructs an image of the calculus during the course of treatment based on the signals from the pressure sensor. An acoustic deflection stage is disposed between the pressure sensor and the focus zone and deflects the low-intensity shock waves to generate a sector scan which covers the focus zone of the high-intensity shock waves. The reception circuit can be operated for producing B-images.

19 Claims, 3 Drawing Sheets

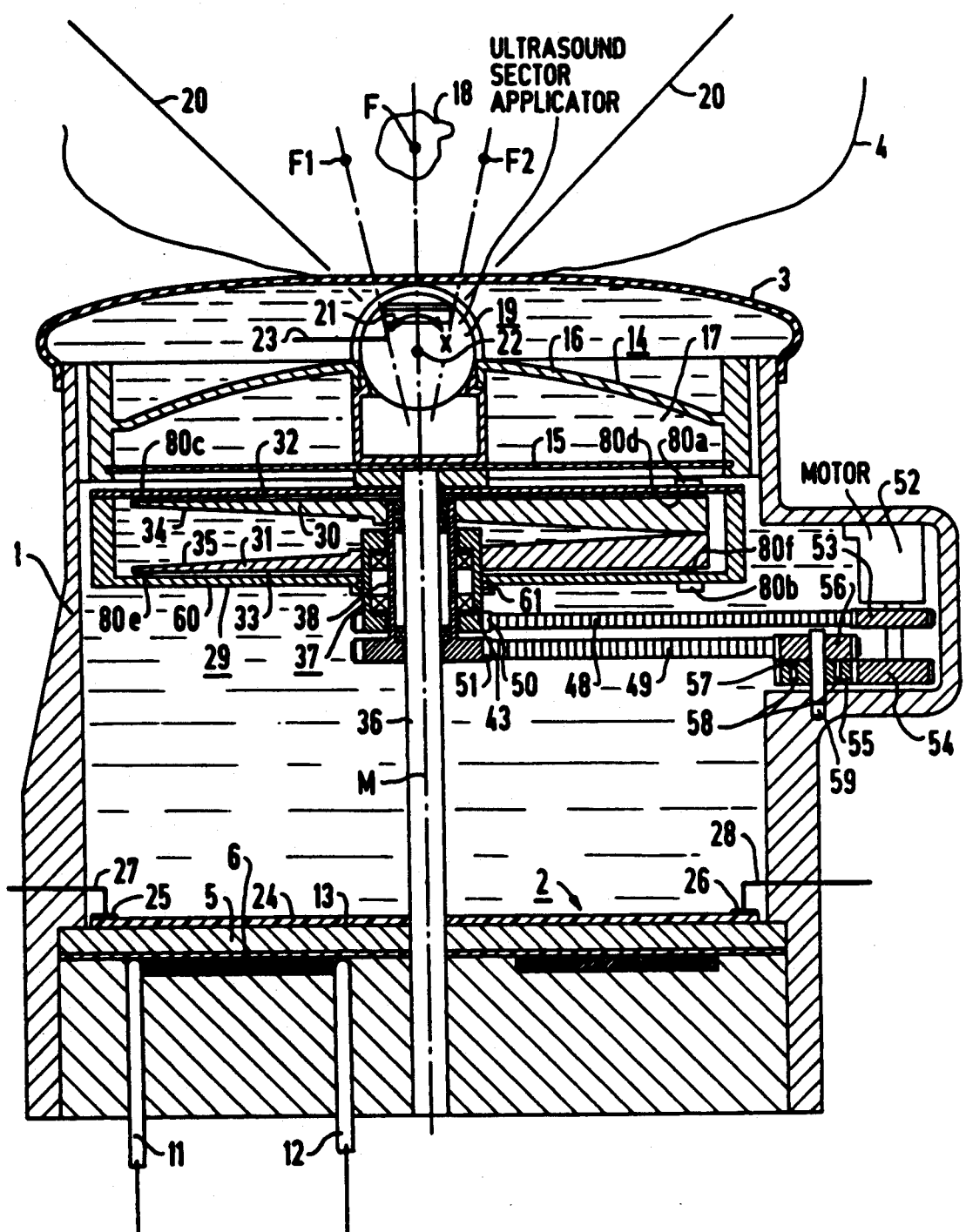
FIG 1
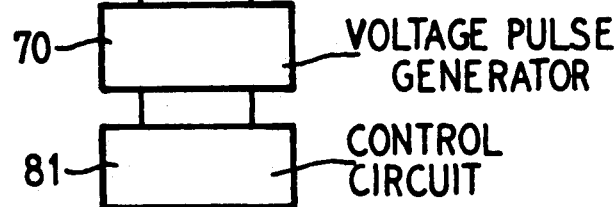

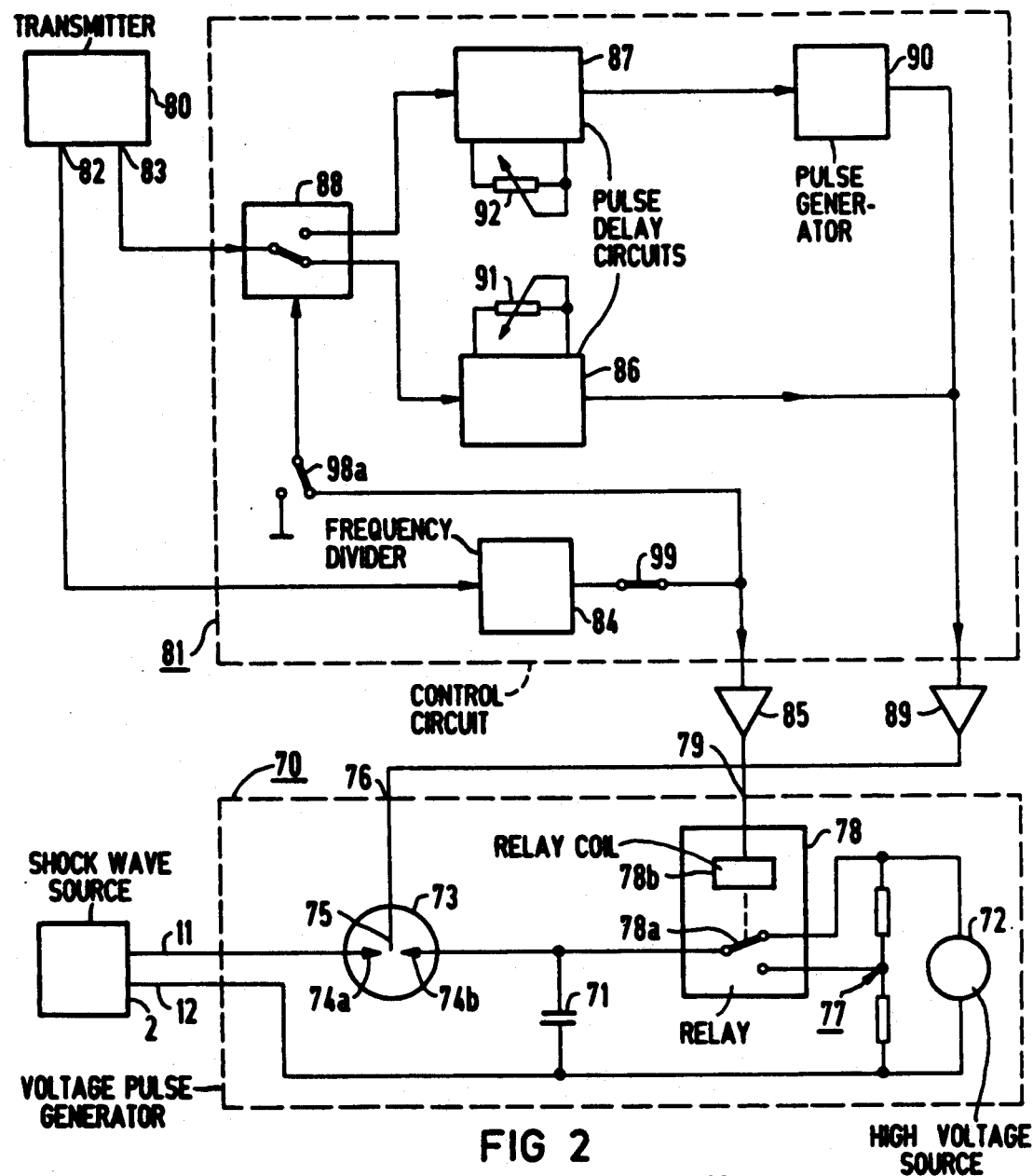
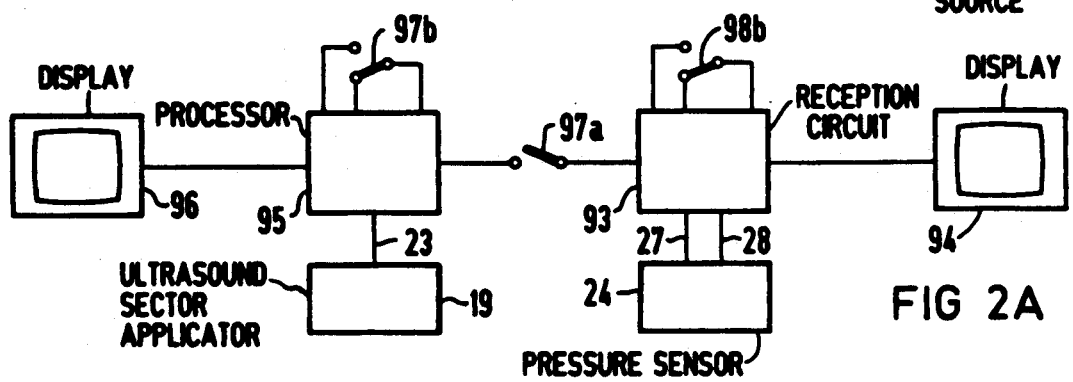
FIG 2
FIG 2A

EXTRACORPOREAL LITHOTRIPSY APPARATUS USING HIGH INTENSITY SHOCK WAVES FOR CALCULUS DISINTEGRATION AND LOW INTENSITY SHOCK WAVES FOR IMAGING

BACKGROUND OF THE INVENTION

1. Field of the Invention

The present invention is directed to an apparatus for extracorporeal lithotripsy which includes a shock wave source that can be selectively driven to generate high-intensity shock waves converging in a focus zone to disintegrate a calculus, and low-intensity shock waves for imaging purposes.

2. Description of Prior Art

In the disintegration of calculi using extracorporeal devices, the location of the calculus to be disintegrated, for example a kidney stone, is first identified in the body of the patient with a suitable locating system. The lithotripsy apparatus is then aligned relative to the body of the patient so that the calculus to be disintegrated is situated in a focus zone of the apparatus. Shock waves are then generated which converge in the focus zone, and which interact with the calculus to generate mechanical stresses which initially decompose the calculus into fragments and into fine grit, with the fragments being made progressively smaller as the treatment continues, until the calculus has completely disintegrated into particles which can be naturally eliminated (excreted).

German AS2722252 discloses an extracorporeal lithotripsy apparatus of the type using a bath of water in which the apparatus and the patient are disposed, the water serving as a propagation medium for the shock waves. In this system, a number of pressure sensors, spatially separated from each other, are provided which permit locating of a calculus to be disintegrated. The pressure sensors are connected to a reception circuit, and register the spherical waves emanating from the calculus after the calculus has been charged with a low-intensity shock wave. This registration is possible as a consequence of known diffraction phenomena. It is also necessary, however, to initially align the apparatus relative to the body of the patient before such a low-intensity shock wave is generated, and for this purpose this known system also includes an ultrasound sector applicator to permit alignment of the patient relative to the stationary shock wave generator so that the calculus is situated in the region of the focus zone of the shock waves. In addition to being used for imaging purposes, the low-intensity shock waves also serve as the means for disintegrating the calculus.

It is usually desirable, however, to obtain information as to the effectiveness of the treatment, i.e., the degree of disintegration of the calculus, during the course of the treatment to permit a determination to be made as to the extent that the calculus has decomposed into fragments or into grit, since the amount of further treatment will be determined on this basis. This is not possible in the system described in German AS2722252, because the ultrasound waves emitted by the ultrasound sector applicator cannot penetrate into a collection of fragments or grit due to their short wavelength. The ultrasound waves are instead reflected at the boundary surface of the collection which faces toward the ultrasound sector application. The individual fragments or grit can therefore not be resolved in an image using this known ultrasound system. It is also not possible to monitor the degree of disintegration using the echo signals of the low-intensity shock waves because the information obtained using the pressure sensors in this known apparatus is essentially identical to that obtained with an ultrasound applicator operated in an A-imaging mode.

SUMMARY OF THE INVENTION

It is an object of the present invention to provide an extracorporeal lithotripsy apparatus having a shock wave source which can be selectively operated to generate high-intensity shock waves converging in a focus zone to disintegrate a calculus, or to generate low-intensity shock waves for imaging purposes, wherein the degree of disintegration, and thus the success of the treatment, can be monitored.

The above object is achieved in an extracorporeal lithotripsy apparatus wherein the pressure sensor is disposed in a shock wave propagating medium between the focus zone and the shock wave source, and has a sensor surface or area which is substantially co-extensive with the cross-sectional area of the shock waves in the region of the pressure sensor. An acoustic deflection stage is disposed in the propagation medium between the pressure sensor and the focus zone. The low-intensity shock waves are deflectable by the acoustic deflection stage to achieve a sector scan which covers the focus zone of the high-intensity shock waves. A reception circuit connected to the pressure sensor can be operated for generating B-images.

The invention is based on the perception that shock waves, including the low-intensity shock waves used for imaging purposes, are significantly lower in frequency (at least in view of their fundamental wave) than the ultrasound waves which are conventionally used for locating purposes. This lower frequency permits shocks waves to "creep" more easily around small objects, thereby permitting imaging of fragments of a calculus disposed in succession in the shock wave propagation direction, and also permitting imaging of the grit which arises during the course of a lithotripsy treatment. Because in the subject matter disclosed herein the low-intensity shock waves can be deflected by the acoustic deflection stage to achieve a sector scan which covers the focus zone, an image comparable to an ultrasound B-image can be generated using the pressure sensor and the reception circuit. This permits the degree of disintegration, and thus the success of the treatment, to be monitored. Although a sharp image is generated only for the region immediately surrounding the focus zone, this is nonetheless adequate to permit an effective monitoring of the degree of disintegration.

Because the pressure sensor is coextensive in area with the cross-sectional area of the shock waves in the region of the pressure sensor, the entire aperture of the shock wave source is used in the generation of an image. The calculus to be disintegrated, and its immediate environment, are thus viewed with the "eye" of the shock wave source, so that information can be obtained which is not obtainable with an ultrasound sector applicator, which scans only a single plane. For example, objects situated in the propagation path of the shock waves, for example, ribs or disturbances such as air bubbles situated in the region of the coupling between the lithotripsy apparatus and the body of the patient, can thus be recognized. Under certain circumstances, however, this information can be conveyed only by the integral image brightness because, as stated above, sharp imaging ensues only in the depth region of the focus zone of the shock wave source. If a calculus to be disintegrated is located using an ultrasound sector applicator, there is also the possibility of demodulating the electrical signals derived from the pressure sensor in such a fashion that a video signal arises which can be mixed with or superimposed on an ultrasound B-image generated using the ultrasound sector applicator, by brightness modulation along the direction of beam propagation. This permits all essential information to be portrayed within a single image.

As noted above, the high-intensity shock waves, which must also traverse the acoustic deflections stage, must converge in a stationary focus zone. In contrast to the low-intensity shock waves, the high-intensity shock waves are not deflected in order to achieve a sector scan. This is achieved by having the focus zone of the high-intensity shock waves lie on the angle bisector of the sector acquired by the sector scan using the low-intensity shock waves. It is also possible, however, to displace the acoustic axis of the high-intensity shock waves, i.e., the axis along which the high-intensity shock waves propagate, by using the acoustic deflection stage. This can be done, for example, to permit the focus zone to follow lateral dislocations of a calculus to be disintegrated which may be caused by the respiratory activity of the patient.

In a preferred embodiment of the invention, the shock wave source can be driven to generate a plurality of low-intensity shock waves at a high repetition rate, for example, 2 kHz, between two successive high-intensity shock waves. This generates a quick image formatting which is accomplished between the two high-intensity shock waves. Moreover, the disintegrating effect of each individual high-intensity shock wave can be monitored, so that the treatment can be immediately ended when the desired result has been achieved, without unnecessarily stressing the patient by the application of further, unneeded high-intensity shock waves.

In another embodiment of the invention, the acoustic deflection stage is formed by a pair of wedge-shaped deflection elements, each consisting of a material having a speed of sound therein which deviates from that of the acoustic propagation medium surrounding the wedge-shaped elements. The wedge-shaped elements are disposed following each other in the propagation direction of the shock waves, and are preferably rotatable around a central rotational axes relative to each other. The wedge-shaped deflection elements have respective limiting surfaces which are inclined by the same angle with respect to the shock wave propagation direction, and which are coextensive with the cross-sectional area of the shock waves in the region of the acoustic deflection stage. The drive system for the wedge-shaped elements can be operated to rotate the elements around the central rotational axes in opposite directions with the same angular speed so that the limiting surfaces come to be disposed at different angular positions, parallel to each other, during a revolution of the elements. U.S. Pat. No. 3,913,061 discloses a deflection system for use in an ultrasound camera including wedge-shaped elements for deflecting the ultrasound waves. The drive system for those wedge-shaped elements in U.S. Pat. No. 3,913,061 can be used to position the wedge-shaped elements in the lithotripsy apparatus disclosed herein. The common, central rotational axes of the wedge-shaped elements is preferably coincident with the central longitudinal axis of the shock wave source.

The pressure sensor may be a piezoelectrically activated plastic foil, for example, a PVDF (polyvinylidenefluoride)-foil. Preferably a membrane driveable in pulsed fashion is provided as the shock wave source, with the plastic foil applied, for example, by gluing, on the side of the membrane facing the focus zone. A simple structural format of the apparatus thereby results. Moreover, degrading effects on the dynamics of the formation of the image, which may be caused by reflections of the echo signals by the shock wave source, are diminished, because such a multiple echo is not present. A complete absence of reflections by the shock wave source at a particular frequency can be achieved by suitable selection of the thickness of the membrane and the material of the membrane with respect to the speed of sound therein. Although reflections will still occur at other frequencies, these reflections will not present a problem if the frequency at which no reflections occur is suitably selected in the context of the other structure and acoustic characteristics of the apparatus.

In another embodiment of the invention, the shock wave source may be a piezoelectric shock wave source, having a first piezoelectric layer for generating the shock waves and a second piezoelectric layer, applied to the first piezoelectric layer, serving as a pressure sensor. The second piezoelectric layer is disposed following the first piezoelectric layer in the direction of shock waves emanating from the first piezoelectric layer. The second piezoelectric layer has a higher resonant frequency than the first piezoelectric layer. As a consequence of non-linearities in the propagation medium and in the body of the patient, the acoustic echo signals are higher in frequency than the fundamental oscillation of the shock wave source. By selecting the second piezoelectric layer to have a higher resonant frequency than the first piezoelectric layer, an adequate sensitivity of the pressure sensor is obtained.

In one embodiment of the invention, the echo signals of the high-intensity or low-intensity shock waves which are received with the pressure sensor can be interpreted in the A-mode with the reception circuit. Because shock waves have a significantly lower amplitude attenuation in comparison to ultrasound waves emanating from a conventional ultrasound locating system, additional information can be acquired using the shock wave echo signals. For example, information identifying the location of a calculus to be disintegrated and identifying the size of the calculus can be obtained on the basis of the level and duration of the echo signal, particularly of a high-intensity shock wave. Moreover, additional information regarding the coupling location between the apparatus and the patient can be acquired with reference to the echo signals of low-intensity shock waves. Given interpretation of the echo signals in the A-mode, it is preferable to use low-intensity shock waves because these will converge in the same focus zone as the high-intensity shock waves, so that a sector scan does not need to be made.

DESCRIPTION OF THE DRAWINGS

FIG. 1 is a side view of an extracorporeal lithotripsy apparatus constructed in accordance with the principles of the present invention.

FIG. 2 is a schematic block circuit diagram of a generator circuit and control circuit for operating the apparatus of FIG. 1.

FIG. 2A is a schematic block diagram for explaining how images obtained using low-intensity shock waves in the apparatus can be combined with an ultrasound image.

DESCRIPTION OF THE PREFERRED EMBODIMENTS

Figure 3:
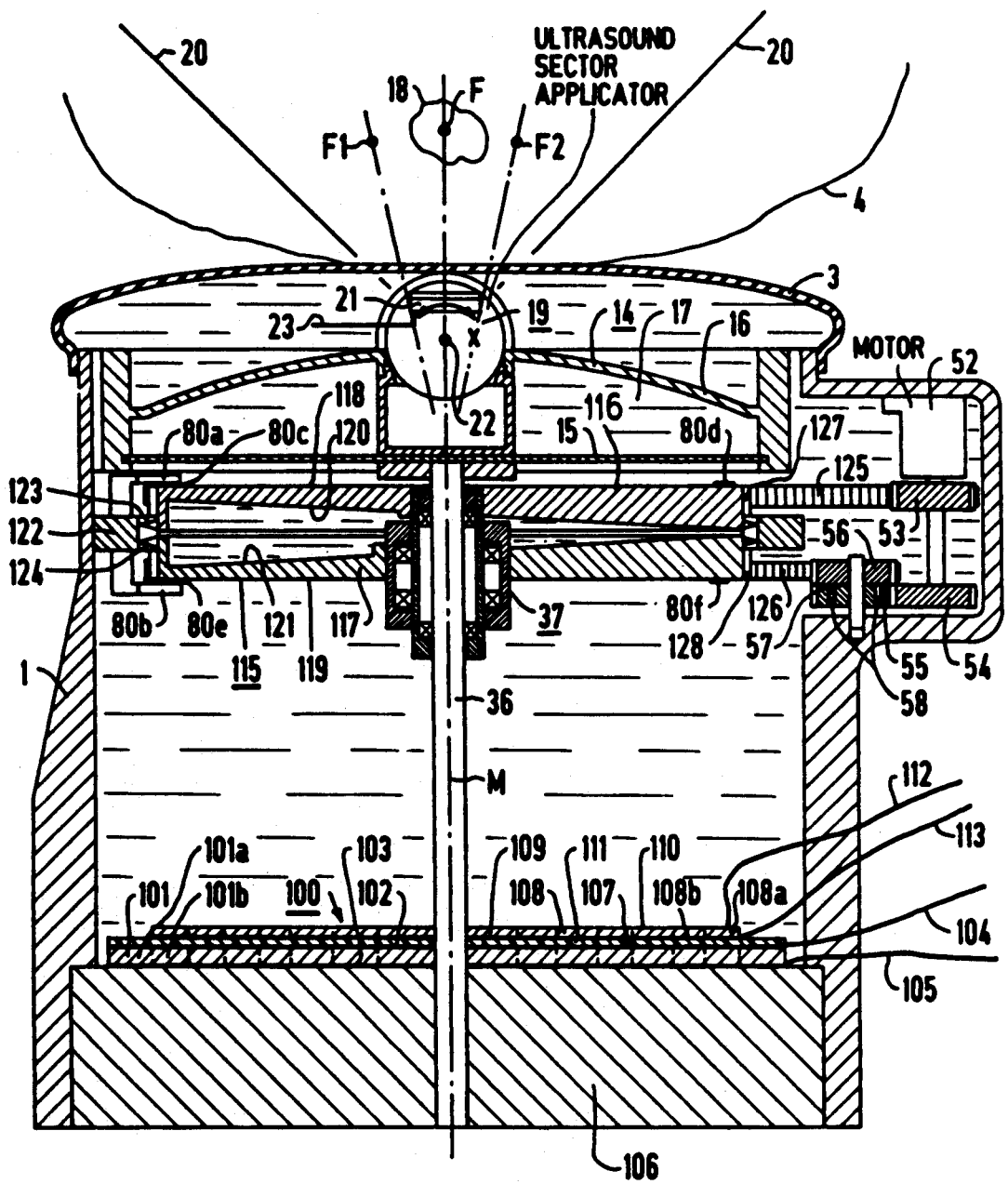
FIG. 3 is a side sectional view of a further embodiment of an extracorporeal lithotripsy apparatus constructed in accordance with the principles of the present invention.

An extracorporeal lithotripsy apparatus constructed in accordance with the principles of the present invention is shown in FIG. 1, wherein the shock wave source generally referenced at 2 is received in one end of a substantially tubular housing 1. The opposite end of the housing 1 is closed with a flexible bellows 3, which permits the apparatus to be pressed against the body of a patient, indicated in cross-section, in which a calculus 18 to be disintegrated is disposed. The interior of the housing 1 is filled with an acoustic propagation medium, such as water.

The shock wave source 2 in the embodiment of FIG. 1 is an electro-dynamic shock wave source, as described in detail in German OS3328051, corresponding to U.S. Pat. No. 4,674,505. The shock wave source 2 includes a planar, circular ring-shaped membrane 5, consisting of electrically conductive material. One side of the membrane 5 faces the propagation medium in the housing 1, and the other side of the membrane 5 faces a flat coil 6. The coil 6 has turns arranged in a spiral, and is chargeable via terminals 11 and 12 with high-voltage pulses from a generator circuit 70 connected to a control circuit 81, both of which are described in detail below.

When the flat coil 6 is charged with a high-voltage pulse, the membrane 5 moves suddenly and rapidly away from the coil 6. As a consequence of this motion, a substantially planar pressure pulse is introduced into the propagation medium, which intensifies into a shock wave during its course through the propagation medium. For simplicity, the term "shock wave" will always be used below, and will be used to encompass the incipient shock wave in the form of a pressure pulse. The region of the membrane 5 which is effective for the emission of shock waves shall be referred to below as the emission area 13 of the membrane 5. The propagation direction of the shock waves in the embodiment of FIG. 1 corresponds to the direction of the center longitudinal axis M of the shock wave source 2.

For focusing the planar shock waves in the manner required to disintegrate a calculus, an acoustic collecting lens 14 is disposed in the propagation medium within the housing 1, between the shock wave source 2 and bellows 3. In the embodiment of FIG. 1 the acoustic collecting lens 14 is a liquid lens. The acoustic collecting lens 14 has an entry face 15 and an exit face 16, between which lens fluid is enclosed. The speed of sound in the lens fluid 17 is different from the speed of sound in the propagation medium surrounding the acoustic collecting lens 14. If, as in the embodiment of FIG. 1, the lens fluid 17 has a speed of sound therein which is lower than the speed of sound in the propagation medium, the acoustic collecting lens 14 must be planoconvex or biconvex. A planoconvex lens 14 is shown in the embodiment of FIG. 1. If a planar shock wave having a wave front proceeding substantially parallel to the entry face 15 passes through the acoustic collecting lens 14, the shock wave is focused to a focus zone F, the focus zone F lying on the axis M of the shock wave source 2. The entry face 15 of the collecting lens 14 preferably consists of polymethylpentene (TPX), and the exit face 16 preferably consists of Teflon ® (polytetrafluoroethylene). The lens fluid 17 is preferably a fluorocarbon liquid, such as Flutec ® PP3 (a liquid chlorofluorcarbon distributed by Kali-Chemie of the Federal Republic of Germany) or Fluorinert ® FC 75 (a perfluoridated chemically and thermally stable liquid distributed by 3M).

To align the apparatus and the body 4 of the patient relative to each other so that the calculus 18 is situated in the focus region F of the shock waves, as shown in FIG. 1, a conventional, schematically illustrated ultrasound sector applicator 19 is provided. The sector applicator 19 provides signals to a conventional ultrasound processing circuit (not shown in FIG. 1), so that ultrasound B-images of a sector-shaped slice of the body 4 of the patient are obtained. The slice is indicated by lines 20 in FIG. 1, and contains the center axis M of the shock wave source 2, and thus also contains the focus zone F. The ultrasound transducer 21 in the ultrasound sector applicator 19 executes an oscillating, pivoting motion in the direction of the double arrow X around an axis 22, as required for scanning the sector limited by the lines 20. The mechanical components of the ultrasound sector applicator 19 are contained in a liquid-filled chamber disposed in the center of the acoustic collecting lens 14. The ultrasound sector applicator 19 is in electrical connection with the aforementioned processing circuitry via electrical lines, with only one line being schematically shown and referenced 23.

A plastic foil 24 is applied, such as by gluing, to that side of the membrane 5 facing toward the propagation medium. The plastic foil 24 is piezoelectrically activated in a region which is coextensive with the emission area 13 of the membrane 5. The plastic foil 24 is preferably a PVDF foil having a thickness, as the thickness of the membrane 5, which is shown exaggerated. The plastic foil 24 is provided with metallizations 25 and 26 to which electrical lines 27 and 28 are attached for providing the necessary electrical contacts for the piezoelectrically activated region. The lines 27 and 28 lead to a reception circuit, described below. The plastic foil 24 serves as a pressure sensor which, in combination with the reception circuit, permits interpretation of the acoustic echo signals of shock waves introduced into the body 6 of the patient. The piezoelectrically activated region of the plastic foil 24 serves as a sensor surface and because it extends over the entire transmission area 13 of the membrane 5, it is coextensive with the cross-sectional area of the shock waves in the region of the plastic foil 24. Because the plastic foil 24 is secured on the membrane 5, its piezoelectrically activated region is disposed on a surface proceeding parallel to the emission area 13.

An acoustic deflection stage 29 is provided within the propagation medium in the housing 1. The deflection stage 29 is disposed between the plastic foil 24 and the focus zone F, such as in front of the acoustic collecting lens 14. The deflection stage 29 permits the shock waves to be deflected so that the focus zone F of the shock waves can be displaced between positions F1 and F2 in a periodically oscillating movement along an approximately arcuate curve lying in a plane containing the center axis M of the shock waves source 2. It is thus possible to deflect the shock waves emanating from the emission area 13 of the shock wave source 2 to achieve a sector scan. The acoustic echo signals of the deflected shock waves can then be interpreted for imaging purposes with the plastic foil 24 serving as a pressure sensor, and with the reception circuit connected thereto. Shock waves which have a lower intensity than those shock waves which are produced for disintegrating the calculus are preferably deflected with the acoustic deflection stage 29 for achieving a sector scan.

The details of the generator 70 for driving the shock wave source 2 are schematically shown in FIG. 2. The generator 70 permits low-intensity shock waves and high-intensity shock waves to be generated, as needed. The generator 70 includes a capacitor 71 which can be charged by a high-voltage source 72. For generating a shock wave, the capacitor 71 is connected to the shock wave source 2 via a triggerable spark gap 73 resulting in a pulse-like discharge. The spark gap 73 has main electrodes 74a and 74b, and a trigger electrode 75 connected to a trigger input 76 of the generator 70. When the trigger electrode 75 is supplied with a trigger pulse, this causes an ionization of the gas molecules situated between the main electrodes 74a and 74b, causing ignition of the spark gap 73.

A voltage divider 77, formed by two high-voltage resistors, is connected in parallel with the high-voltage source 72. A contact 78a of a high-voltage relay 78 permits the capacitor 71 to be connected either directly to the high-voltage source 72 or to a tap of the voltage divider 77. Dependent on switching position of the high-voltage relay 78, the capacitor 71 can be charged either to the full voltage output of the high-voltage source 72 for generating a high-intensity shock wave, or to a voltage which is reduced in magnitude by the divider ratio of the voltage divider 77 to produce a low-intensity shock wave. The high-voltage relay 78 has an excitation coil 78b which is connected to control input 79 of the generator 70.

To operate the apparatus so that the high-intensity shock waves converge in a stationary focus zone and the low-intensity shock waves are deflected with the weight required for achieving a sector scan, a transmitter 80, coupled to the acoustic deflection stage 29, and the control circuit 81 are provided. The control circuit 81 uses periodic signals from the transmitter 80 to generate the signals required for the trigger input 76 and for the control input 79 of the generator 70.

The transmitter 80 has a first output 82 at which a pulse appears for each displacement, in either direction of the focus zone between the positions F1 and F2. A second output 83 is provided at which a pulse appears each time the focus zone F assumes a defined position. The signals available at the outputs 82 and 83 are supplied to the control circuit 81.

The control circuit 81 includes a digital frequency divider circuit 84 having an input connected to the output 82 of the transmitter 80. In the most simple case, the frequency divider circuit 84 has a division factor of two, so that a signal which changes its logic state with each displacement of the focus zone from F1 toward F2, and from F2 toward F1, is present at its output. The output signal of the frequency divider circuit 84 is supplied via an amplifier 85 to the excitation windings 78b of the high-voltage relay 78. When the output signal of the frequency divider circuit 84 has the value of a logic "0" the contact 78a of the high-voltage relay 78 assumes the switch position shown in FIG. 2, i.e., the capacitor 71 is charged to the full high-voltage supplied by the high-voltage source 72, as required for generating a high-intensity shock wave. When the output signal of the frequency divider circuit 84 has the value of a logic "1", the contact 78a of the high-voltage relay 78 changes its switch position so that the capacitor 71 is connected to the tap of the high-voltage divider 77, as required for generating low-intensity shock waves.

The control circuit 81 also includes two pulse delay circuits 86 and 87 whose inputs are alternately connectable to the output 83 of the transmitter 80 with an electronic switch 88. The switch 88 is actuated by the output signal of the frequency divider circuit 84. When the output signal of the frequency divider circuit 84 has the value of a logic "0" the electronic switch 88 assumes the switch position shown in FIG. 2, i.e., the pulse delay circuit 86 is connected to the output 83 of the transmitter 80. When the output signal of the frequency divider circuit 84 assumes the value of a logic "1" the switch 88 changes its switch position and the pulse delay circuit 87 is connected to the output 83 of the transmitter 80.

The pulse delay circuits 86 and 87 delay a pulse arriving from the output 83 of the transmitter by a defined pulse delay time, which is different in the two pulse delay circuits 86 and 87. From the output of the pulse delay circuit 86, the delayed pulse proceeds via an amplifier 89 to the trigger input 76 of the generator 70, causing ignition of the spark gap 73, and this the generation of a shock wave. Because the electronic switch 88, as the high-voltage relay 78, is actuated by the output signal of the frequency divider circuit 84, a pulse from the delay circuit 86 triggers a high-intensity shock wave. The pulse delay circuit 87 serves the purpose of triggering low-intensity shock waves.

A pulse generator 90 is connected between the pulse delay circuit 87 and the amplifier 89, which generates a rapid sequence of, for example, 250 pulses when a pulse from the delay circuit 87 is supplied to its input. The sequence of pulses extends over a time span which is significantly shorter than the duration of the signal appearing at the output 82 of the transmitter 80. Whereas only individual high-intensity shock waves are generated, a plurality of low-intensity shock waves, corresponding to the number of pulses from the pulse generator 90, is generated between two successive high-intensity shock waves. These low-intensity shock waves are deflected in the manner of a sector scan by the deflection stage 29, which causes a periodic deflection of the acoustic axis of the shock wave source 2. The delay time of the pulse delay circuit 87 is selected so that the generation of the low-intensity shock waves occurs during a movement of the focus zone between the positions F1 and F2, or vice versa. This results in the scanning of a sector having an angle bisector corresponding to the center axis M of the shock wave source 2. The delay time of the pulse delay circuit 86 is selected so that the high-intensity shock waves converge in a stationary focus zone which preferably lies on the center axis of the apparatus. As indicated by adjustment resistors 91 and 92 respectively connected to the pulse delay circuits 86 and 87, the pulse delay times can be adjusted to adapt the delay times to individual requirements.

The acoustic echo signals of the low-intensity shock waves are picked up by the plastic foil 24, and are interpreted in a reception circuit 93, as shown in FIG. 2, so that an image similar to an ultrasound B-image is obtained, which is shown on a display 94 connected to the reception circuit 93. The reception circuit 93 is a conventional ultrasound processor circuit to which the echoes from the low intensity shock waves are fed instead of conventional ultrasound echoes.

FIG. 2 also schematically indicates the connection of the ultrasound sector applicator 19 to an ultrasound processing circuit 95 for generating ultrasound B-images, which are shown on a display 96. Switches 97a and 97b are connected to each other so that, when moved to the switch position other than the position shown in FIG. 2A, the signals generated by the reception circuit 93 are supplied via the switch 97a to the processor 95. The processor 95 is simultaneously switched to an operating mode by the switch 97b so that information acquired by the plastic foil 24 and the reception circuit 93 are included, with brightness modulation along the appropriate beam direction, in the ultrasound B-image generated by the ultrasound sector applicator 19 and the processor 95.

A further operating mode is available in an embodiment wherein the switches 98a and 98b are connected to each other in a manner different from that described above, so that when the switch 98a is actuated, the output signals from the frequency divider circuit 84 are prevented from reaching the electronic switch 88. Instead, the switch 98a is connected to ground, in the opposite switch position from that shown in FIG. 2, so that a potential corresponding to a logic "0" is continuously supplied to the electronic switch 88. This means that the output 83 of the transmitter 80 will continuously be connected to the pulse delay circuit 86. The high-voltage relay 78, however, continues to be switched at the frequency of the output of the frequency divider circuit 84, via the control input 79. A high-intensity shock wave and a low-intensity shock wave are thus generated in alternation, and converge, also in alternation, in the same stationary focus zone. The reception circuit 93 is switched by the switch 98b to evaluate the acoustic echo signals of the low intensity shock wave received by the plastic foil 24 in the A-mode, so that an image similar to an ultrasound A-image of the focus zone of the high-intensity shock waves is shown on the display 94. The switching of the reception circuit 93 from B- to A-mode to generate an A-image instead of a B-image is accomplished in the same manner as in conventional ultrasound processor circuits.

If the switch 99 is opened, the output signals from the frequency divider circuit 84 do not reach the control input 79, so that only high-intensity shock waves are generated. These high-intensity shock waves will also generate acoustic echo signals, so that images similar to ultrasound A-images are produced with the plastic foil 24 and the reception circuit 93, which are shown on the display 94.

If the frequency divider circuit 84 has a division factor other than two, for example, a division factor of eight, and if the switch 99 is in the switch position shown in FIG. 2, seven high-intensity shock waves are initially generated before the generation of the sequence of low-intensity shock waves, or the generation of a single low-intensity shock wave.

As can be seen in FIG. 1, the deflection stage 29 includes a pair of circular disc-shaped elements 30 and 31 having coinciding center axes which also coincide with the center axis of the apparatus. Each of the elements 30 and 31 has a respective planar limiting surface 32 or 33 which proceeds at a right angle relative to the center axis M. Each element 30 and 31 also has a respective planar limiting surface 34 or 35, which is inclined by an angle relative to the center axis M. The surfaces 34 and 35 are inclined by the same angle, and the elements 30 and 31 have the same dimensions, and are thus of an identical wedge-shape. The diameter of the elements 30 and 31 is selected so that they are coextensive with the cross-sectional area of the shock waves in the region of the deflection stage 29. The elements 30 and 31 are seated so as to be independently rotatable on an axle 36 aligned with the center axis M. The elements 30 and 31 are mounted on the axle 36 by a bearing assembly 37. The bearing assembly 37 includes a rotatable tube 38 attached to the element 30 and a separately rotatable tube 43 attached to the element 31. The tube 43 has a lower projection with teeth 50 which engage corresponding teeth of a belt 48, and the tube 38 has a lower projection having teeth 51 which engage similar teeth in a belt 49. The belt 48 is also entrained about a gear 53, of the same diameter as the lower projection on the tube 38, and the belt 49 is entrained around a gear 56, of the same diameter as the lower projection on the tube 43. The gear 54 engages a spur gear 55 of the same diameter in torsional connection with the gear 56. Both the gears 55 and 56 are rotatable around a jackshaft 59 in the housing 1. The gears 53 and 54 are driven an electric motor 52, contained in a projection of the housing 1. The elements 30 and 31 will thus be rotated in opposite rotational directions with the same angular speed by the motor 52 via the belts 48 and 49. During a complete revolution of the elements 30 and 31, there will be two positions wherein the limiting surfaces 34 and 35 are parallel to each other. The phase relation, i.e., the angles at which the two positions occur at which the surfaces 34 and 35 are parallel, can be varied by varying the angular position of the gear 55 relative to the gear 56. This can be done as shown in FIG. 1 by providing the gear 55 with a plurality of bores 58 which may be spaced, for example, at intervals of 15° at the face of the gear 55 facing the gear 56. The gear 56 is provided with pins 57 which are received in the bores 58 so that a desired phase relationship can be obtained. The pins 57 can also serve to make the torsional connection between the gears 55 and 56.

The elements 30 and 31 may consist of polymethylpentene (TPX) and are surrounded by a stationary housing 60 of the same material. A sealing ring 61 closes the interior of the housing 60 liquid-tight. The interior of the housing 60 contains a fluorine-carbon liquid, for example, Flutec ® PP3 or Fluorinert ® FC 75. The speed of sound in the material comprising the elements 30 and 31 is approximately 2000 m/s, whereas the speed of sound in the liquid in the interior of the housing 60 and surrounding the elements 30 and 31 is approximately 600 m/s. As a consequence of these different speeds of sounds, shock waves which traverse the deflection stage 29 are deflected. It would be possible to mount the elements 30 and 31 directly in the propagation medium which fills the housing 1. If that propagation medium is water, however, by arranging the elements 30 and 31 in a fluorocarbon liquid a more pronounced deflection occurs, since the speed of sound in water is approximately 1500 m/s, and therefore a greater difference in the speeds of sound occurs between the elements 30 and 31 and the fluorocarbon liquid, then between the elements 30 and 31 and water.

If the elements 30 and 31 are in the position as shown in FIG. 1, the focus zone of the shock waves is displaced by the greatest possible amount, so that it is situated at the position F1. If, proceeding from the position shown in FIG. 1, the elements 30 and 31 are rotated in directions opposite to each other, the focus zone of the shock waves gradually migrates to the center axis M of the shock wave source 2. When the elements 30 and 31 have executed one-fourth of a revolution, the limiting surfaces 34 and 35 are parallel to each other, and the focus zone of the shock waves is at the position F on the center axis M. During the next quarter revolution of the elements 30 and 31, the focus zone migrates to the other extreme position F2, at which point the elements 30 and 31 will be in a position which is a mirror image of the position shown in FIG. 1. After a further quarter revolution of the elements 30 and 31, the limiting surfaces 34 and 35 will again be parallel to each other, so that the focus zone is again on the center axis M. When the elements 30 and 31 have completed a revolution, the focus zone will again be at the position F1. This is repeated for each full revolution of the elements 30 and 31. It is thus clear that the acoustic deflection stage 29 permits the focus zone to be deflected to generate a sector scan, as discussed above.

To chronologically match the output of the high-intensity or low-intensity shock waves with the motion of the elements 30 and 31, and thus with the motion of the focus zone of the shock waves, the aforementioned transmitter, referenced 80 in FIG. 2, is provided. The components of the transmitter 80 are shown in FIG. 1, but since they are spatially separated it is not possible to generally reference the transmitter in FIG. 1. In FIG. 1, the transmitter includes two Hall generators 80a and 80b, one of which is stationarily attached to the base of the housing 60 and the other which is stationarily attached to the top or cover of the housing 60. The transmitter also includes four permanent magnets, permanent magnets 80c and 80d being attached to the element 30, and permanent magnets 80e and 80f being attached to the element 31. The magnets are disposed diametrically opposite each other on the respective elements 30 and 31, so that they are moved past the Hall generators 80a and 80b during the revolution of the elements 30 and 31. For each revolution of the elements 30 and 31 the Hall generator 80a supplies two pulses which are available at the output (FIG. 2) of the transmitter 80. The pulse signal at the output 83 (FIG. 2) of the transmitter 80 is formed by the time difference between the pulses at the output 82 and pulses supplied by the Hall generator 80b. This occurs each time the focus zone assumes a defined position, this position being dependent on the phase relation of the elements 30 and 31 which has been selected. It is therefore necessary to match the delay times of the pulse delay circuits 86 and 87 to the selected phase relation of the elements 30 and 31, which is accomplished by the aforementioned adjustment resistors 91 and 92. The adjustment is made so that the high-intensity shock waves converge at the selected stationary focus zone, and the sector scan of the low-intensity shock waves covers the desired sector.

A further embodiment of the invention is shown in FIG. 3, which departs from the embodiment of FIG. 1 only in the structuring of the acoustic deflection stage and the shock waves source. Other components already discussed in connection with FIG. 1 are identical in FIG. 3, and are provided with the same reference symbols.

In the embodiment of FIG. 3, a piezoelectric shock wave source generally referenced at 100 is provided instead of the electro-dynamic shock wave source 2 of FIG. 1. The shock wave source 100 includes a first piezo-ceramic layer 101 which may consist, for example, of barium-titanate. The respective major faces of the first layer 101 are covered with respective metal layers 102 and 103, and which serve to connect the first layer 101 to lines 104 and 105 which lead to a generator as described in FIG. 2. The first layer 101 accordingly serves the purpose of generating high-intensity or low-intensity shock waves, and thus has its metal layer 103 attached to a damping element 106. The metal layer 102, connected to the first layer 101, forms the emission area 107 of the shock wave source 100. A second piezo-electric layer 108, which may also consist of barium-titanate, is applied to the emission area 107. The second layer 108 is also provided with metal layers 109 and 110, which may also consist of lead for electrical contacting, and an insulating layer 111 is disposed between the metal layers 102 and 109. The second layer 108 function as a pressure sensor for the reception of the acoustic echo signals of the shock waves emanating from the emission area 107, and accordingly as connected to a reception circuit corresponding to the reception circuit 93 of FIG. 2. This connection is made via lines 112 and 113 attached to the metal layers 109 and 110. The second piezo-ceramic layer 108 has a considerably lower thickness then the first piezo-ceramic layer 101, and thus has a significantly higher resonant frequency than the first layer 101. Both the layers 101 and 108 may consist of individual piezo-ceramic elements 101a, 101b, etc. and 108a, 108b, etc., arranged in mosaic fashion, as schematically indicated in FIG. 3.

The acoustic deflection stage 115 provided in the embodiment of FIG. 3 has two wedge-shaped elements 116 and 117, again formed of polymethylpentene (TPX). In contrast to the deflection stage 29 in the embodiment of FIG. 1, the elements 116 and 117 are not received in their own housing. In the embodiment of FIG. 3, the limiting surfaces 118 and 119 of the elements 116 and 117 proceed at a right angle relative to the center axis M of the shock wave source 100, and are directly in contact with the propagation medium, such as water, contained in the housing 1. A fluorocarbon liquid is present only between the limiting surfaces 120 and 121 which face each other, and which are inclined by the same angle relative to the center axis M. In order to prevent the liquid between the surfaces 120 and 121 from mixing with the propagation medium contained in the housing 1, an annular wall 122, connected to the housing 1, is provided which surrounds the elements 116 and 117 at their circumferences. The interior of the annular wall 122 engages sealing rings 123 and 124 respectively attached to the circumferential edges of the elements 116 and 117.

The drive of the elements 116 and 117 is achieved with respective toothed belts 125 and 126 which engage teeth 127 and 128 respectively disclosed at the circumferences of the elements 116 and 117.

Hall generators 80a and 80b are also provided in the embodiment of FIG. 3, which are attached to the annular wall 122 and interact with permanent magnets 80c and 80d attached to the element 116 and permanent magnets 80e and 80f attached to the element 117.

The acoustic deflection stage 115 has a distance from the emission area of the shock wave source 100 approximately corresponding to the focal length of the acoustic collecting lens 14. This assures that multiple echoes appearing between the emission area 107 of the shock wave source 100 and the acoustic deflection stage 115 are displaced to the lower edge of the image generated by the low-intensity shock waves. A corresponding relationship is also selected in the apparatus shown in the embodiment of FIG. 1.

In the embodiment of FIG. 3, a piezo-electrically activated plastic foil can be provided as the pressure sensor, instead of the second piezo-ceramic layer 108, as in the embodiment of FIG. 1. If this is done, however, the plastic foil should be disposed at a distance of approximately two through three centimeters away from the emission area 107, to avoid image-degrading influences of multiple echoes arising in the shock wave source 100.

Although the embodiments of FIGS. 1 and 3 show shock wave sources two and 100 having respective planar emission areas 13 and 107, it is possible to replace those sources with sources having curved emission faces, so that the shock waves emanating therefrom are already focused. It would then be unnecessary to provide the acoustic collecting lens 14.

Although modifications and changes may be suggested by those skilled in the art, it is the intention of the inventors to embody within the patent warranted hereon all changes and modifications as reasonably and properly come within the scope of their contribution to the art.

We claim as our invention:

1. An extracorporeal lithotripsy apparatus for treatment of a calculus in the body of a patient, comprising:
   means for generating shock waves propagating in a propagation direction and converging in a focus zone;
   means including a shock wave propagation medium for coupling shock waves generated by said means for generating shock waves into the body of said patient;
   means for selectively driving said means for generating shock waves to generate high intensity shock waves converging in a focus zone of high intensity shock waves for disintegrating said calculus or for generating low-intensity shock waves for producing an image of said focus zone of high-intensity shock waves;
   pressure sensor means disposed in said propagation medium for measuring echoes in the form of pressure fronts having a cross-section caused by reflection of said shock waves for generating electrical signals corresponding thereto, said pressure sensor means having a surface active for sensing pressure which is co-extensive with the cross-section of said echoes in the region of said surface;
   acoustic means through which said flow intensity shock waves pass for deflecting said low-intensity shock waves, when generated, for conducting a sector scan which includes said focus zone of high-intensity shock waves; and
   reception means connected to said pressure sensor means for generating said image of said focus zone of high-intensity shock waves from said electrical signals in the form of a B-image.

2. An apparatus as claimed in claim 1 wherein said means for selectively driving said means for generating shock waves includes means for generating a plurality of low-intensity shock waves at a high repetition rate between two successive high-intensity shock waves.

3. An apparatus as claimed in claim 1 wherein said acoustic deflection means comprises:
   first and second deflection elements consisting of material having a speed of sound therein different from the speed of sound in said propagation medium and disposed following each other in said propagation direction of said shock waves, each of said first and second deflection elements having first and second surfaces, said respective first surfaces of said first and second deflection elements being inclined by the same first angle relative to said propagation direction and the respective second surfaces of said first and second deflection elements being inclined by the same second angle with respect to said propagation direction, said first and second surfaces being substantially coextensive with the cross-sectional area of the shock waves in the region of the acoustic deflection means; and
   means for rotating said deflection elements around a central axis in opposite directions with the same angular speed so that the respective second surfaces of said first and second deflection elements assume two angular positions at which said second surfaces are parallel to each other during each revolution of said first and second deflection elements.

4. An apparatus as claimed in claim 3 further comprising:
   transmitter means disposed adjacent said acoustic deflection means for generating a signal when said deflection elements are disposed at a defined position relative to each other;
   means in said means for selectively driving said means for generating shock waves for generating a plurality of low-intensity shock waves at a high repetition rate between two successive high-intensity shock waves, said means for generating a plurality of low-intensity shock waves being enabled by said signal from said transmitter means; and
   delay means connected between said transmitter means and said means for generating a plurality of low-intensity shock waves for delaying said signal from said transmitter means by a delay time selected to achieve said sector scan.

5. An apparatus as claimed in claim 3, wherein said two angular positions of said deflection elements at which said second faces are parallel to each other define a phase relationship between said deflection elements, and said acoustic deflection means further comprising means for varying said phase relationship between said first and second deflection elements.

6. An apparatus as claimed in claim 1, wherein said means for generating shock waves comprises:
   a planar shock wave source which generates planar shock waves; and
   an acoustic collecting lens which focuses said planar shock waves in said focus zone, said acoustic collecting lens being disposed such that said acoustic deflection means is disposed between said pressure sensor and said acoustic collecting lens.

7. An apparatus as claimed in claim 6, wherein said acoustic collecting lens has a focal length, and wherein said acoustic deflection means is disposed a distance from said planar shock wave source at least equalling the focal length of said acoustic collecting lens.

8. An apparatus as claimed in claim 1, wherein said means for generating shock waves includes a membrane which is rapidly moveable to create a shock wave, and wherein said pressure sensor means is a piezoelectric plastic foil attached to a side of said membrane facing said focus zone.

9. An apparatus as claimed in claim 1, wherein said means for generating shock waves includes a first piezoelectric layer for generating said shock waves and wherein said pressure sensor comprises a second piezoelectric layer attached to said first piezoelectric layer following said first piezoelectric layer in the direction of shock wave propagation, said second piezoelectric layer having a higher resonant frequency than said first piezoelectric layer.

10. An apparatus as claimed in claim 1, further comprising means for selectively alternatively operating said reception means as a means for generating an image of said focus zone of high-intensity shock waves from said electrical signals in the form of an A-image.

11. An apparatus as claimed in claim 1, wherein said means for generating shock waves has a longitudinal axis coinciding with said propagation direction, and wherein said acoustic deflection means comprises:
   first and second deflection elements operable in combination to deflect said focus zone laterally with respect to said longitudinal axis of said means for generating shock waves, said deflection elements consisting of a material having a speed of sound therein which is different from the speed of sound in the propagation medium;
   a housing disposed in said propagation medium and containing said first and second deflection elements and a further propagation medium, said further propagation medium having a speed of sound therein which differs from the speed of sound in said propagation medium, said housing being sealed to prevent mixing of propagation medium and said further propagation medium; and
   means for rotating said first and second deflection elements relative to each other to laterally shift said focus zone.

12. An apparatus as claimed in claim 11, wherein said propagation medium, said further propagation medium, and said material comprising said first and second deflection elements have respective speeds of sound therein such that the difference between the speed of sound in said further propagation medium and the speed of sound in said material comprising said deflection elements is greater than the difference between the speed of sound in said propagation medium and the speed of sound in said deflection elements.

13. An apparatus as claimed in claim 12, wherein said deflection elements consists of polymethylpentene, wherein said propagation medium is water and wherein said further propagation medium is a fluorocarbon liquid.

14. An apparatus as claimed in claim 1, wherein said means for generating shock waves has a longitudinal axis coinciding with said propagation direction, and wherein said acoustic deflection means comprises:
   first and second deflection elements operable in combination to laterally deflect said focus zone relative to said longitudinal axis, said first and second deflection elements consisting of material having a speed of sound therein differing from the speed of sound in said propagation medium;
   an annular wall disposed in said propagation medium and surrounding said deflection elements;
   means for creating a seal between said annular wall and said deflection elements thereby creating a volume between said deflection elements separated from said propagation medium;
   a further propagation medium filling said volume, said further propagation medium having a speed of sound therein differing from the speed of sound in said propagation medium; and
   means for rotating said deflection elements to laterally deflect said focus zone.

15. An apparatus as claimed in claim 14, wherein said propagation medium, said further propagation medium, and said material comprising said first and second deflection elements have respective speeds of sound therein such that the difference between the speed of sound in said further propagation medium and the speed of sound in said material comprising said deflection elements is greater than the difference between the speed of sound in said propagation medium and the speed of sound in said deflection elements.

16. An apparatus as claimed in claim 15, wherein said deflection elements consists of polymethylpentene, wherein said propagation medium is water and wherein said further propagation medium is a fluorocarbon liquid.

17. An extracorporeal lithotripsy apparatus for treatment of a calculus in the body of a patient, comprising:
   means for generating shock waves propagating in a propagation direction and converging in a focus zone;
   means including a shock wave propagation medium for coupling shock waves generated by said means for generating shock waves into the body of said patient;
   means for selectively driving said means for generating shock waves to generate high-intensity shock waves converging in a focus zone of high-intensity shock waves for disintegrating said calculus or for generating low-intensity shock waves for producing an image of said focus zone of high-intensity shock waves;
   pressure sensor means disposed in said propagation medium for measuring echoes in the form of pressure fronts having cross-section caused by reflection of said shock waves for generating electrical signals corresponding thereto, said pressure sensor means having a surface active for sensing pressure which is co-extensive with the cross-section of said echoes in the region of said surface;
   acoustic means, disposed in said shock wave propagation medium between said means for generating shock waves and said focus zone of high-intensity shock waves, for deflecting said low-intensity shock waves, when generated, for conducting a sector scan which includes said focus zone of high-intensity shock waves; and
   reception means connected to said pressure sensor means for generating said image of said focus zone of high-intensity shock waves from said electrical signals in the form of a B-image.

18. An apparatus as claimed in claim 17 wherein said means for selectively driving said means for generating shock waves includes means for generating a plurality of low-intensity shock waves at a high repetition rate between two successive high-intensity shock waves.

19. An apparatus as claimed in claim 17, further comprising means for selectively alternatively operating said reception means as a means for generating an image of said focus zone of high-intensity shock waves from said electrical signals in the form of an A-image.

* * * * *